US005752929A

United States Patent [19]
Klatz et al.

[11] Patent Number: 5,752,929
[45] Date of Patent: *May 19, 1998

[54] METHOD OF PRESERVING ORGANS OTHER THAN THE BRAIN

[75] Inventors: Ronald M. Klatz; Robert M. Goldman, both of Chicago, Ill.

[73] Assignee: Life Resuscitation Technologies, Inc., Chicago, Ill.

[*] Notice: The term of this patent shall not extend beyond the expiration date of Pat. No. 5,395,314.

[21] Appl. No.: 476,719

[22] Filed: Jun. 7, 1995

Related U.S. Application Data

[63] Continuation of Ser. No. 383,240, Feb. 3, 1995, Pat. No. 5,584,804, which is a continuation-in-part of Ser. No. 69,916, Jun. 1, 1993, Pat. No. 5,395,314, which is a continuation-in-part of Ser. No. 886,041, May 19, 1992, Pat. No. 5,234,405, which is a division of Ser. No. 595,387, Oct. 10, 1990, Pat. No. 5,149,321.

[51] Int. Cl.$^6$ ............................................. A61M 21/00
[52] U.S. Cl. .................. 604/51; 604/24; 604/28; 128/898; 128/DIG. 13
[58] Field of Search .................... 604/23–28, 49, 604/52, 4–6, 113, 114; 651/105–107; 128/898, DIG. 12, DIG. 13, DIG. 27, 913

[56] References Cited

U.S. PATENT DOCUMENTS

| | | |
|---|---|---|
| 1,682,344 | 8/1928 | Lesieur . |
| 1,916,658 | 7/1933 | Davidson . |
| 3,406,531 | 10/1968 | Swenson et al. . |
| 3,632,473 | 1/1972 | Belzer et al. . |
| 4,378,797 | 4/1983 | Osterholm . |
| 4,393,863 | 7/1983 | Osterholm . |
| 4,445,500 | 5/1984 | Osterholm . |
| 4,451,251 | 5/1984 | Osterholm . |
| 4,657,532 | 4/1987 | Osterholm . |

(List continued on next page.)

FOREIGN PATENT DOCUMENTS

| | | |
|---|---|---|
| 265082 | 4/1988 | European Pat. Off. . |
| 297723 | 1/1989 | European Pat. Off. . |
| 221361 | 4/1985 | Germany . |
| 1213276 | 8/1989 | Japan . |
| 760972 | 9/1980 | U.S.S.R. . |
| 1632428 | 3/1991 | U.S.S.R. . |
| WO 96/32074 | 10/1996 | WIPO . |
| WP 96/32157 | 10/1996 | WIPO . |

OTHER PUBLICATIONS

"Cerebral Blood Flow, Vasoreactivity, and Oxygen Consumption During Barbiturate Therapy in Severe Traumatic Brain Lesions", by Carl–Henrik Nordström, MD et al., J. Neurosurg. vol. 68, Mar. 1988, pp. 424–431.

(List continued on next page.)

Primary Examiner—Michael Powell Buiz
Assistant Examiner—Chalin Smith
Attorney, Agent, or Firm—Oliff & Berridge, PLC

[57] ABSTRACT

The invention discloses methods for preserving organs in brain-dead humans or cadavers which allows additional time for the organs to remain viable such that they may be harvested for subsequent transplantation. This invention also discloses methods for preserving and/or resuscitating organs in live (nonbrain-dead) patients, allowing for additional time to stabilize the patient's condition. The methods include the steps of instrumentizing (e.g., catheterizing, cannulating, injecting, etc.) the vessels or tissues around the organ, or the organ itself sought to be preserved and/or resuscitated, the body cavity, or cavities of the body, and introducing a temperature-controlled solution to preserve and/or resuscitate the organ(s). The temperature-controlled organ preservation solution includes components such as oxygen carrying agents, antioxidants, tissue damage reversing and protecting agents, carrier vehicles, diluents, nutrients, and anti-coagulating agents. A device which performs this method is also disclosed. This device includes a fluid reservoir, an oxygen tank, a heat exchanger and removable catheter lines.

34 Claims, 2 Drawing Sheets

U.S. PATENT DOCUMENTS

| | | |
|---|---|---|
| 5,028,588 | 7/1991 | Hoffman et al. ............................. 514/6 |
| 5,036,097 | 7/1991 | Floyd et al. ............................. 514/400 |
| 5,047,395 | 9/1991 | Wu et al. ............................. 514/2 |
| 5,085,630 | 2/1992 | Osterholm . |
| 5,130,230 | 7/1992 | Segall et al. ............................. 435/1 |
| 5,145,771 | 9/1992 | Lemasters et al. . |
| 5,149,321 | 9/1992 | Klatz et al. . |
| 5,200,176 | 4/1993 | Wong et al. . |
| 5,216,032 | 6/1993 | Manning . |
| 5,217,860 | 6/1993 | Fahy et al. . |
| 5,234,405 | 8/1993 | Klatz et al. . |
| 5,383,854 | 1/1995 | Safer et al. . |
| 5,385,821 | 1/1995 | O'Dell et al. ............................. 435/1 |
| 5,395,314 | 3/1995 | Klatz et al. . |
| 5,437,633 | 8/1995 | Manning . |

OTHER PUBLICATIONS

"At Surgery's Fontier: Suspended Animation", by Elisabeth Rosenthal, *The New York Times*, Nov. 13, 1990, pp. C1, C12.

"Randomized Clinical Study of Thiopental Loading in Comatose Survivors of Cardiac Arrest", *The New England Journal of Medicine*, vol. 314, No. 7, Feb. 13, 1986, pp. 397–403.

"Current Concepts in Brain Resuscitation", By Mark C. Rogers, MD, *Journal of the American Medical Association*, vol. 261, No. 21, pp. 3143–3147.

"Cerebrovascular Hypoxic and Autoregulatory Responses During Reduced Brain Metabolism", by Judith H. Donegan et al., *The American Physiological Society*, (1985), vol. 249, pp. H421–H429.

"Regional Cerebral Blood Flow In Normal Blood Circulated and Perfluorocarbon Transfused Rats", *Advances in Experimental Medicine and Biology*, (1986), vol. 200, pp. 59–65.

"Protection from Cerebral Air Emboli with Perflurorocarbons in Rabbits", Bruce D. Spiess, MD, et al., *Stroke*, vol. 17, No. 6, Nov.–Dec. 1986, pp. 1146–1149.

"Free Radicals and Myocardial Ischemia and Reperfusion Injury", by Paul J. Simpson, *J. Lab. Clin. Med.*, Jul. 1987, pp. 13–30.

"Increases in Brain Tumor and Cerebral Blood Flow by Blood–Perfluorochemical Emulsion (Fluosol–DA) Exchange", by Shoju Hiraga et al., *Cancer Research*, vol. 47, No. 12, pp. 3296–3302.

"Polarographic Cerebral Oxygen Availability, Fluorocarbon Blood Levels and Efficacy of Oxygen Transport by Emulsions", by Leland C. Clark, Jr. et al., *Biomaterials*, 16(1–3), (1988), pp. 375–393.

"The Nature of Fluorocarbon Enhanced Cerebralk Oxygen Transport", by Leland C. Clark, Jr. et al., *Advances in Experimental Medicine and Biology*, vol. 248, pp. 341–355.

"Easier Breathing in RDS", *Medical Tribune*, Jan. 11, 1990, p. 2.

"Cerebral Ischemic Injury", by Blaine C. White, *Emergency Medicine, A Comprehensive Study Guide*, 1988 pp. 9–10.

"90s Could See Brain Injury Reversal", *American Medical News*, Nov. 17, 1989, p. 66.

"Cooling Brain May Limit Stroke Damage", *American Medical News*, Nov. 17, 1989, p. 66.

"Drug May Preserve Heart Tissue After Attack", *New York Times*, Sep. 5, 1989, p. 3.

"Radical Therapy", By Karen Wrig, *Scientific American*, Sep. 1987.

"Diseases of the Central Nervous System", Asbury, McKhann, McDonald, pp. 1071 and 1083.

"Resuscitation of the Rabbit Brain After Acute complete Ischemia Lasting Up To One Hour: Pathophysiological and Pathomorphological Observations", by Ryszard Plunta, *Resuscitation* 15, (1987), pp. 267–287.

"The Use of Blood Substitutes for Whole Body Perfusion in Ultra–Profound Hypothermic Cardiac Arrest", Amr M. Elrifai et al., *Annals of Clin. and Lab. Sceince*, vol. 20, No. 4, Jul.–Aug. 1990, p. 292.

"Nutritional Aspects of Ambulatory Care", *American Family Physicians*, vol. 42, No. 3, Sep. 1990, pp. 557–558.

"In Situ Cadaver Kidney Perfusion", by Robert T. Schweizer et al., *Transplantation, Official Journal of the Transplantation Society*, vol. 32, No. 6, Dec. 1981, pp. 482–484.

"In situ kidney preservation for transplantation with use of profound hypothermia (5 to 20° C.) with an intact circulation", by A.R. Moossa et al., *Surgery*, vol. 79, No. 1, Jan. 1976, pp. 60–64.

"Extracorporeal perfusion for obtaining postmortem homografts", by T.L. Marchioro, M.D. et al., *Surgery*, vol. 54, No. 6, Jul.–Dec., 1963, pp. 900–911.

"Use of Extracorporeal Cadaver Perfusion for Preparation of Organ Homografts", by T.L. Marchioro, M.D., *Surgical Forum*, vol. XIV, Oct., 1963, pp. 174–176.

"Donor Core–Cooling Provides Improved Static Preservation for Heart–Lung Transplantation", by Charles D. Fraser, Jr. M.D., *The Annals of Thoracic Surgery*, vol. 45, No. 3, Mar. 1988, pp. 253–257.

"Long–Life Dream —A Window to Survival", *Longevity*, Dec. '89/Jan. '90 (1–page).

"The Art of Staying Alive", by Vic Sussman, *U.S. News & World Report*, Oct. 18, 1993, pp. 70–71.

"New Device May Save Brains Being Lost in Cardiac Arrest", Dr. Ronald Klatz et al., Nov. 4 and 11, 1989.

Robert J. White, Preservation of Cerebral Function During Circulatory Arrest and Resuscitation: Hypothermic Protective Considerations, Resuscitation, I, pp. 107–115, 1972.

METHOD OF PRESERVING ORGANS OTHER THAN THE BRAIN

CROSS-REFERENCES TO RELATED APPLICATIONS

This application is a continuation of application Ser. No. 08/383,240, filed Feb. 3, 1995, now U.S. Pat. No. 5,584,804 which is a continuation-in-part of application Ser. No. 08/069,916, filed Jun. 1, 1993, now U.S. Pat. No. 5,395,314, which is a continuation-in-part of application Ser. No. 07/886,041, filed May 19, 1992, now U.S. Pat. No. 5,234,405, which is a Divisional of application Ser. No. 07/595,387, filed Oct. 10, 1990, now U.S. Pat. No. 5,149,321.

FIELD OF THE INVENTION

The present invention relates generally to treating ischemic and anoxic brain injuries associated with cardiac arrest. More particularly, the present invention provides an apparatus and method for resuscitation of the brain and maintenance of viability during trauma or other periods of decreased blood flow, allowing the health professional extra time to restore blood circulation and body functions. With the present invention, the brain and associated neurologic tissues remain intact, throughout attempts to restart the victim's heart and restore circulation, allowing the victim increased chances of survival with less chance of permanent brain damage.

The present invention also provides an apparatus and method for preserving organs in brain-dead patients or cadavers, which keeps the requisite organs viable for extended time periods. With this invention, the organs may be preserved such that they are suitable for subsequent harvesting and transplantation.

BRIEF DESCRIPTION OF THE PRIOR ART

During cardiac arrest, the heart ceases to pump blood. Subsequently, there is no circulation, and the brain fails to receive freshly oxygenated blood. Without a steady supply of oxygenated blood, the brain will cease to function.

Current resuscitation techniques for cardiac arrest have been directed almost exclusively towards the heart. However, even with methods such as cardiopulmonary resuscitation (CPR), patient survival rates are low. In hospitals and clinics with advanced CPR and life support systems, the survival rate is normally around 14%. Outside of hospital settings, the survival rate is about 5%.

Among cardiac arrest victims overall, less than 10% survive neurologically intact and without significant brain damage. The other approximately 90% either die or sustain some neurologic injury from ischemia, (i.e., lack of blood flow to the brain), or anoxia (i.e., lack of oxygen to the brain). Such frequency of neurologic injury occurs because after cardiac arrest, basic cardiopulmonary resuscitation and advanced life support techniques, such as CPR, closed heart cardiac chest massage, and electroshock treatments, typically require fifteen to twenty minutes to regain circulation from a failed heart. Reversible neurologic damage begins as early as four minutes and irreversible neurologic damage begins as early as six minutes after circulation stops. To combat this potential neurologic injury, initial resuscitation efforts need to be directed toward reviving the brain in addition to resuscitating the heart.

As indicated above, anoxic and ischemic brain injuries from cardiac arrest result in damage to the brain and associated neurologic tissues after about four minutes. In contrast, the heart can survive intact up to approximately four hours after cardiac arrest. The short viability of brain tissue upon deprivation of oxygenated blood is a result of the requirement of high amounts of nutrients for tissue maintenance. Brain tissue uses almost all of the nutrients supplied by the circulating blood for maintenance and has very little remaining for storage. Absent blood flow to the brain, the small amount of stored nutrients is rapidly exhausted. Once exhausted, brain oxygen content rapidly depletes. This oxygen depletion is traumatic and causes a series of reactions in the oxygen starved brain tissue cells. These reactions produce free radical ions, primarily consisting of the superoxide radical $O_2$. These free radicals complex with proteins in the brain and associated neurologic tissues, altering respiration, energy transfer and other vital cellular functions, and irreversibly damaging these tissues.

Prior efforts at resuscitating the brain have involved highly invasive treatments, intruding physically into the brain itself. Such invasive techniques are described in U.S. Pat. Nos. 4,378,797 and 4,445,500 issued to Osterholm. These patents describe a stroke treatment method which is a direct physical intrusion into the brain itself. In this method, an opening is drilled directly through the skull through the brain into the pons or brain ventricles. These areas are then directly cannulated and flooded with room temperature oxygenated perfluorocarbons. These entering perfluorocarbons mix with cerebral spinal fluid, whereby they are carried throughout the brain and associated neurologic tissues through channels within the central nervous system, sometimes referred to as t "third circulation." Excess fluid is drained through an opening invasively placed in the cisterna magna of the brain.

This stroke treatment method has several drawbacks. This method must be performed in a surgical environment by a skilled surgical team. It cannot be done by a single person with basic medical training. It cannot be done in the field or other emergency type settings. The device used in performing this stroke treatment is not portable. Additionally, since this procedure is invasive (drilling directly into the brain), there is a high risk of mechanical damage to the brain and associated neurologic tissues. Finally, the treatment fluid used contains essentially perfluorocarbons. It lacks any agents needed to inhibit free radical damage.

Additionally, despite the dramatic success and increase in the number of organ transplants, there remains a massive shortfall of organs suitable for donation and subsequent transplant. The demand for organs remains greater than the supply. As a result, thousands of people unnecessarily die.

This is an irony because of the potential abundance of suitable organs. Specifically, more than 1.5 million Americans who die from trauma, accidents or cardiac arrest with organs suitable for transplant, could easily have their organs salvaged.

Present salvaging techniques include putting the organ in ice after having been perfused in a Collins solution. This Collins solution mimics the internal environment of the cells, which form the organ tissue, and keeps the organ viable for approximately forty-eight hours.

In most cases, these present methods do not permit sufficient time to transfer a suitable viable organ to the needy recipient. This is because organs deprived of oxygen nutrient rich blood flow in a body at normal body temperature suffer irreversible damage and injury in just a few hours or less. For example, the heart must be salvaged almost immediately, while the kidneys must be salvaged within one to three hours.

Under present circumstances, the time prior to that which a potentially transferable organ may be salvaged is usually delayed. This occurs because the brain-dead person must first be brought to a hospital. Alternatively, a person dying outside a hospital or other clinical setting must first be brought to a morgue and be pronounced dead. The family must then sign organ donation forms. Only after the brain-dead person has been brought to a hospital and the organ donation procedures are complete, may a surgical team be permitted access to the body to harvest the viable organs for transplant. This procedure takes time to a point where organs are irreversibly damaged or are no longer viable.

It is therefore an object of this invention to non-invasively treat ischemic and anoxic brain injuries immediately upon cardiac arrest whereby resuscitation efforts are applied in time for a patient to survive neurologically intact. By directing resuscitating efforts to immediately treating the brain, the present invention allows medical personnel substantial additional time (beyond the critical four minute window) to regain the failed heart's circulation without the patient suffering neurologic damage.

It is also an object of the invention to provide a method of treating ischemic and anoxic brain injuries suffered upon cardiac arrest so as to inhibit free radical chemical species from complexing with proteins in the brain and neurologic tissue to avoid permanent irreversible damage.

It is another object of the invention to resuscitate the brain by establishing a non-invasive, artificial circulation of synthetically oxygenated blood to the brain.

It is yet another object of the invention to prevent and reverse potential damage to the brain and associated neurologic tissue suffered as a result of ischemic injury due to cardiac arrest, major trauma, suffocation, drowning, electrocution, blood loss and toxic poisoning from substances including carbon monoxide and cyanide.

It is a further object of the invention to provide a device for treating the aforementioned injuries, which is suited for field as well as clinical use and that can be operated by a single person with minimal medical training and experience.

It is still another object of the invention to provide a solution capable of inhibiting free radical ions from complexing with proteins in brain and associated neurologic tissue, and capable of protecting these tissues and reversing injuries to these tissues, thereby expanding the brain's critical four minute viability window.

It is still another object of this invention to provide a method of preserving organs in their viable states in brain-dead patients or cadavers, in order for organ harvesting, whereby the harvested organs are suitable for transplantation.

It is still another object of the invention to prevent and reverse potential damage to a brain-dead patient's or cadaver's organs prior to organ harvesting such that the harvested organs remain viable for harvesting, whereby they are suitable for transplantation.

SUMMARY OF THE INVENTION

The present invention focuses on initial resuscitation efforts toward resuscitating the brain due to its short viability, rather than the heart. The invention includes a non-invasive method which reverses and inhibits neurologic damage, and resulting ischemic and anoxic injury upon cardiac arrest. The method includes establishing an artificial circulation by catheterizing the circulatory system in both external carotid arteries, to deliver essential treatment components in a synthetic brain resuscitation solution to the brain. Once catheterized, the brain is driven into a submetabolic coma as barbiturates are introduced through the catheter. This coma lowers the brain's metabolism and decreases free radical production, while keeping its tissues viable. The brain is oxygenated by introducing temperature-controlled perfluorocarbons, which are supersaturated with oxygen.

These perfluorocarbons act as a blood substitute and transport oxygen in a manner similar to hemoglobin. Free radical damage is inhibited by introducing antioxidants, free radical scavengers. The antioxidants complex with the ionic $O_2^-$ and prevent the ions from complexing with proteins in brain tissue, which is a cause of irreversible damage. Protecting and reversing neurologic damage is accomplished by introducing Lazaroids, an experimental drug class now being developed by the Upjohn Pharmaceutical Company of Kalamazoo, Mich.

All of the above-mentioned compositions are included in a single brain resuscitation solution. This brain resuscitation solution is delivered to the brain in a chilled condition. The fluid is chilled by cooling it to a temperature sufficiently low to hypothermically shock the brain. At this point, the brain's metabolism is slowed and free radical production decreases. The brain is additionally cooled externally with natural or synthetic ice packs around the patient's head.

Once the procedure is complete, continuing efforts are then made to resuscitate the heart and restore the circulation. This can be achieved by drug administration, CPR (manual and mechanical), chest compression, and the like.

Additionally, the present invention discloses a method of resuscitating or preserving organs (collectively known as organ preservation) in a brain-dead patient or cadaver prior to their harvesting for transplant, such that a viable organ is transplanted. The method includes establishing an artificial circulation within the organ by catheterizing a major blood or lymph vessel supplying the organ or organ tissue parenchyma, to deliver essential treatment components in a synthetic solution to it. The solution is cooled below body temperature and introduced through the catheter. The solution includes components which serve to lower the organ's metabolism and decrease free radical production, while keeping the organ viable. Specifically, one such solution includes temperature-controlled perfluorocarbons, which are supersaturated with oxygen. These perfluorocarbons oxygenate the organ by acting as a blood substitute, transporting oxygen in a manner similar to hemoglobin. Free radical damage is inhibited by introducing antioxidants, free radical scavengers. The antioxidants complex with the ionic $O_2^-$ and prevent the ions from complexing with proteins in the tissue, which is a cause of irreversible damage. Further tissue damage protection is accomplished by introducing Lazaroids, an experimental drug class now being developed by the Upjohn Pharmaceutical Company of Kalamazoo, Mich.

All of the above-mentioned compositions are included in a solution similar to that described above for brain resuscitation. The only significant difference is that barbiturates, which induce a coma in the brain, while permissible, are preferably not used in organ preservation as this result is not needed in this instance. Similar to the above-mentioned brain resuscitation solution, the organ preservation and resuscitation solution (hereinafter organ preservation solution), is chilled by cooling it to a sufficiently low temperature to inhibit degenerative metabolism of the organ. When the organ's metabolism is slowed, free radical production decreases.

Once this procedure is complete the organ will remain viable, such that harvesting and subsequent transplantation may take place at a later time. The harvested organ will have sustained minimal, if any damage, and the transplant recipient will be able to resume a normal life.

The present invention includes a device for delivering the aforementioned brain resuscitation or organ preservation solutions. The device can be adapted for clinical or field use. This device includes a reservoir for holding brain resuscitation or organ preservation solution which communicates with an oxygen tank and a heat exchanger. Upon activation, the oxygen is released into the reservoir, oxygenating the brain resuscitation or organ preservation solution. The oxygenated solution is then pumped from the reservoir to the heat exchanger, where it is cooled. When brain resuscitation is desired, the cooled solution is then introduced to the patient's circulatory system through the catheterized carotid arteries or other blood vessels and directed toward the brain. Alternately, in organ preservation, the cooled solution is introduced into blood or lymph vessels supplying the organ, the organ itself or the tissue surrounding the organ. For example, with the pancreas, the intestine, a surrounding tissue, would provide organ preservation solution to the pancreas by capillary circulation.

BRIEF DESCRIPTION OF THE DRAWINGS

For a more complete understanding of the invention reference should be made to the drawings wherein.

DETAILED DESCRIPTION OF THE DRAWINGS

Figure 1:
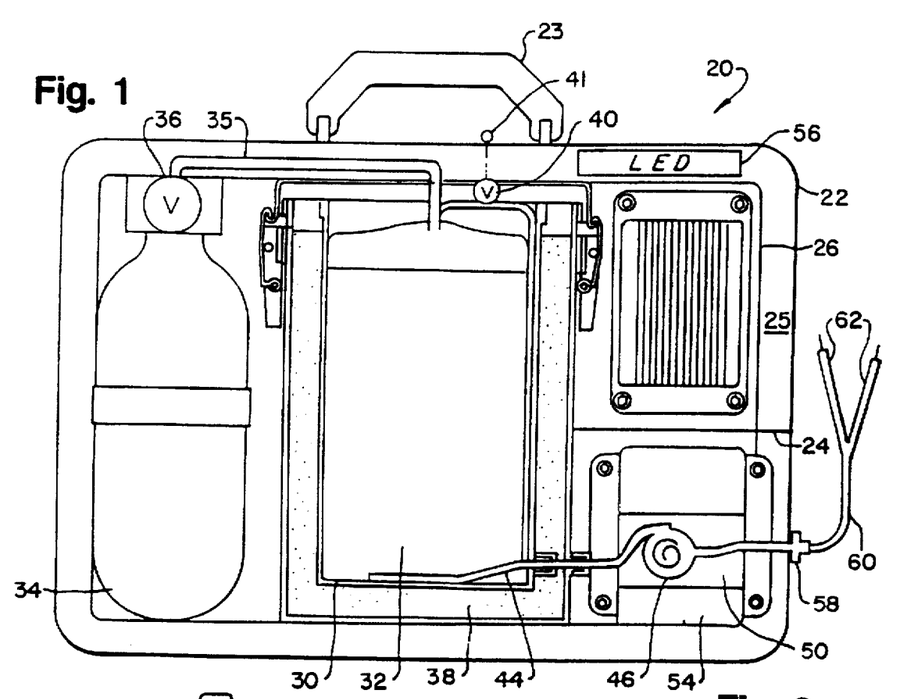
FIG. 1 is a front view of the portable brain resuscitation/ organ preservation device of the invention illustrating the internal components.
Figure 2:
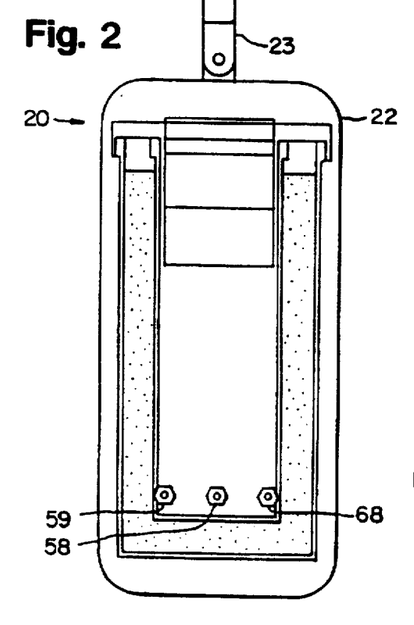
FIG. 2 is a side view of the portable brain resuscitation/ organ preservation device of FIG. 1.

Referring to FIGS. 1 and 2, the brain resuscitation/organ preservation device 20 of this embodiment of the invention is semi-automatic. It includes an outer casing 22 with a handle 23 and a window 24. The window 24 is located within a first side 25 which has a greater width than length. The casing 22 includes an inner chamber 26. This inner chamber 26 contains components which include a reservoir 30, an oxygen tank 34, a heat exchanger 38, a pump 46, a logic control unit 50, and a power source 54.

The reservoir 30 holds the brain resuscitation or organ preservation solution. The solution of this invention is a fluid mixture of various components and is packaged in premixed, premeasured canisters, for a single immediate use. These canisters can be replenished (refilled) and exchanged for continued life support. The specific components are discussed below in accordance with the methods of the invention. Preferably, this reservoir 30 is adapted to hold three liters of fluid contained within replaceable canisters 32. The preferred canisters are clear plastic bags, such that fluid depletion in the reservoir 30 can be viewed through the window 24. However, these canisters can be rigid containers, made of opaque material.

An oxygen tank 34, adjustable to various pressures, communicates with reservoir 30 through a first conduit 35. Oxygen tank 34 is sealed by a valve 36, which is opened once the device 20 is activated. Tank 34 is preferably a cylinder ten inches tall by four inches in diameter, containing oxygen pressurized to at least 17 psig.

A heat exchanger 38 capable of controlling the fluid's temperature, surrounds reservoir 30. Preferably the heat exchanger cools by undergoing an internal endothermic reaction, once a charging valve 40 is opened when a charging handle 41 on the device is activated. The exchanger contains Ammonium Nitrate and water, which are initially separate. Upon activation, these chemicals contact each other, reacting endothermically, causing the heat exchanger to cool. Additionally, the heat exchanger's cooling can be accomplished by carbon dioxide (dry ice), freon or a mechanical cooling device.

A second conduit 44 extends from the reservoir and communicates with a valve controlled pump 46, capable of pumping at various rates, directions (forward and reverse) and modes, in communication with a logic control unit 50. The pump 46 and the logic control unit 50 are both powered by an energy source 54. However, the device is suitable for an electric adapter. A battery pack is the preferred energy source 54. The logic control unit 50 includes (not shown) an oxygen pressure sensor, a fluid mass flow sensor, a fluid volume indicator and regulator, a fluid pressure indicator and regulator, a fluid temperature indicator and regulator, a fluid temperature indicator with feedback to a mass sensor, and a timing device for estimating the time the fluid in the reservoir will be depleted at a given mass flow. The logic control unit 50 can control the rate, direction and mode of pumping, i.e. forward or reverse, continuous or pulsatile. One example of a pulsatile rate and mode would be that which simulates the pulsed flow of a beating heart. Measurements from logic control unit 50 are displayed on an LED digital display 56. Digital display 56 preferably shows the temperature and flow rate of the brain resuscitation solution.

The second conduit 44 extends through the pump 46 and logic control unit 50 and terminates in a side opening 58 on the device 20. Preferably, this side opening 58 is on the side 66 adjacent to the longitudinal side 25. Side opening 58 is capable of attaching to catheter lines 60 to permit brain resuscitation solution to enter the patient's circulatory system, through catheters 62 placed into a single, but preferably both, external or internal carotid arteries. Similarly, side opening 58 is capable of attaching to catheter lines 60 to permit organ preservation solution to enter the patient's circulatory system, through catheters 62 placed into a single vessel near the organ sought to be preserved, the organ itself or tissues surrounding the organ.

With respect to catheters 62, one way balloon tipped catheters are preferred. The balloons generally inflate upon activation to block potential reverse blood and brain resuscitation or organ preservation fluid flow toward the heart (except in organ preservation where the heart is being resuscitated and/or preserved). Catheters 62 may also be dual or multiple lumen catheters.

Additionally, it is preferred that this adjacent side 66 also contain openings for venting excess oxygen 68 and for oxygen intake 69. This oxygen intake can be from the atmosphere or from adjunct oxygen sources.

Upon activating the brain resuscitation or organ preservation device, the oxygen tank valve 36 opens and pressurized oxygen is released from the oxygen tank 34 into contact with the brain resuscitation or organ preservation fluid, thereby oxygenating it. The heat exchanger 38 is activated by releasing the charging valve 40. Once activated, the oxygenated solution in the reservoir is cooled. This cooled solution moves through a second conduit 44, drawn by sufficient pressure from the oxygen tank 34 into a logic control unit 50, powered by an energy source 54, such as a battery pack. A pump 46, within this logic control unit 50 further moves the chilled oxygenated solution through this second conduit. Solution then enters 35 a catheter line 60, attached to an opening 58 in device 20 whereby it is delivered to the brain or organ through the catheters 62.

The preferred embodiment of the brain resuscitation/ organ preservation device is relatively small. It is portable, suitcase-like in appearance, and suitable for field use, such as in ambulances, battlefields, athletic fields, aircraft, marine vehicles, spacecraft, emergency treatment facilities, and the like. It is lightweight and can be carried directly to the patient. In one example of the device the outer casing measures twenty inches by eighteen inches by fifteen inches and weighs approximately thirty pounds.

Figure 3:
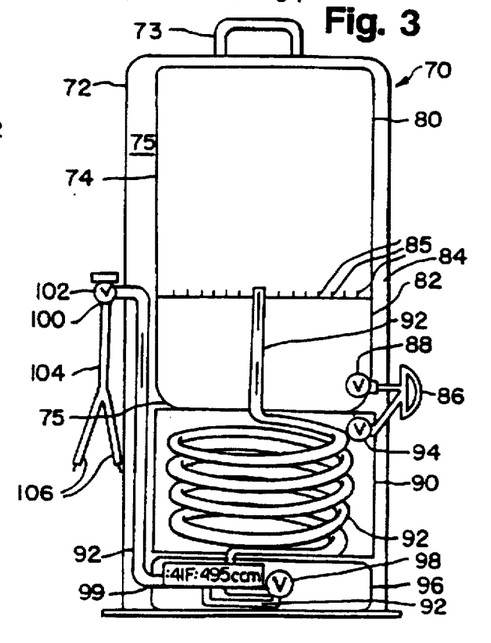
FIG. 3 is a front view of a second embodiment of the portable device shown in FIG. 2.

FIG. 3 is a second embodiment of the brain resuscitation/ organ preservation device 70. This embodiment is mechanical. It is manually activated and is fully operative under pneumatic power generated by pressurized oxygen. Device 70 includes an outer casing 72 with a handle 73 and preferably a window 74, located in a first side 75 having a greater length than width. The outer casing 72 includes an inner chamber 76. This inner chamber 76 contains components which include a reservoir 80, an oxygen tank 82, a heat exchanger 90, and a logic control unit 96.

The reservoir 80 holds the brain resuscitation or organ preservation solution of the invention. The brain resuscitation or organ preservation solution is a mixture of various components and is packaged in premixed, premeasured canisters, for a single immediate use. These canisters can be replenished (refilled) and exchanged for continued life support. The specific components of the brain resuscitation or organ preservation solution are discussed below in accordance with their respective methods. Preferably, reservoir 80 is adapted to hold four to ten liters of solution contained within replaceable canisters 84. The preferred canisters are clear plastic bags through which the fluid depletion in the reservoir 80 can be viewed through the window 74.

Reservoir 80 communicates with an oxygen tank 82 through channels 85, which open when a charging handle 86 is pulled. Oxygen tank 82 is adjustable to various pressures and is sealed by a valve 88 on the charging handle 86. The oxygen is pressurized to at least 17 psig.

Reservoir 80 also communicates with a heat exchanger 90, capable of controlling the solution's temperature, through a conduit 92. Similar to that of the first embodiment, the preferred heat exchanger cools by undergoing an internal endothermic reaction, as explained with the first embodiment above. Heat exchanger 90 communicates with the charging handle through a valve 94, which when activated by pulling, initiates cooling.

Conduit 92 extends through the heat exchanger 90 into a logic control unit 96. Logic control unit 96 includes (not shown) an oxygen pressure sensor, a fluid mass flow sensor, a fluid pressure indicator and valve 98 for regulating fluid pressure and flow, a fluid temperature indicator and regulator, a fluid temperature indicator with feedback to a mass sensor, and a timing device for estimating the time fluid in the reservoir 80 will be depleted at the current mass flow. Measurements from this logic control are displayed on an LED digital display 99. Digital display 99 shows the brain resuscitation or organ preservation fluid temperature and flow rate.

Conduit 92 extends from the logic control unit 96, to a terminal point 100 outside the device 70. A high pressure fluid coupling valve 102 is at this terminal point 100. The valve 102 is opened when the device 70 is activated. This terminal point 100 is suitable for attachment of catheter line 104 and subsequent catheters 106.

As with device 20, one way balloon tipped catheters are preferred in alternate device 70. Upon activation the balloon portion of the catheter inflates, blocking possible reverse blood and brain resuscitation or organ preservation solution flow toward the heart.

Additionally, it is preferred that device 70 contain openings for venting excess oxygen and for oxygen intake.

This oxygen intake can be from the atmosphere or adjunct oxygen sources.

Device 70 is activated when the user pulls the charging handle 86. This action opens a valve 88 on the oxygen tank 82, releasing pressurized oxygen, which moves through channels 85 into the reservoir 80 and into contact with the brain resuscitation or organ preservation solution thereby oxygenating the fluid solution. The pressure from this released oxygen drives the oxygenated solution into conduit 92 which passes through a heat exchanger 90, thereby cooling the solution. Once the cooled oxygenated fluid solution leaves the heat exchanger 90, it continues in conduit 92 through the logic control unit 96.

Once past the logic control unit 96, the solution moves through this conduit 92 until it terminates in a high pressure solution coupling valve 102 outside of the device 70. When the high pressure valve 102 is open, and 25 catheters 106 are coupled to this terminal conduit end 100, brain resuscitation or organ preservation solution can enter the patient's circulatory system. The oxygen pressure preferred is at least 17 psig, sufficient to drive this brain resuscitation or organ preservation solution 30 from the reservoir 80 into the brain or organ respectively.

Other alternative embodiments may have two reservoirs. This would be especially useful in brain resuscitation. The first reservoir would be kept at body temperature or slightly cooler whereby this "warm" brain resuscitation solution is available to flood the brain and quickly diffuses in it, whereby the blood-brain barrier is crossed. The second reservoir is available to deliver "cool" (approximately forty degrees fahrenheit) resuscitation solution, chilled by the heat exchanger, for the purpose of inducing hypothermic shock (discussed below).

Another alternative embodiment of the two-reservoir device, quite advantageous for brain resuscitation, includes a first reservoir containing unoxygenated fluid, kept at body temperature or slightly below. A bolus of this "warm" unoxygenated solution is initially delivered to the brain, so as to prevent an oxidative burst of free radicals. The second reservoir is available to deliver cool (approximately 40 degrees F.) oxygenated resuscitation solution to the brain for the purpose of inducing hypothermic shock (discussed below). The above-described heat exchangers cool the solution, while oxygenating the solution occurs through either of the embodiments disclosed in FIGS. 1-3, as either of these embodiments is modified such that only this second reservoir communicates with the oxygen source. The "cool" oxygenated resuscitation solution is delivered to the brain shortly after the initial "warm" unoxygenated solution has been delivered.

Still additional alternative embodiments may use preoxygenated solution in the reservoirs. Reservoirs containing preoxygenated fluid solution eliminate the need for oxygen tanks as these devices have sufficient power (enhanced electronics and powerful pumps), capable of moving the brain resuscitation solution from the reservoir in the device to the brain.

While these two preferred embodiments are portable devices particularly suited for portable, field use, they are also suited for stationary, clinical use. Should a clinical device be desired, these two portable embodiments could be made larger and modified accordingly for such use.

In operation, the brain resuscitation/organ preservation device supplies treatment solution for the accompanying resuscitation or preservation methods respectively. As previously stated, one aspect of the invention comprises a method of treating anoxic and ischemic injuries suffered as a result of cardiac arrest, suffocation, drowning, electrocution, losses of circulation, strokes, bodily injuries, toxic (carbon monoxide, cyanide, etc.) poisoning, and associated major trauma.

Figure 4:
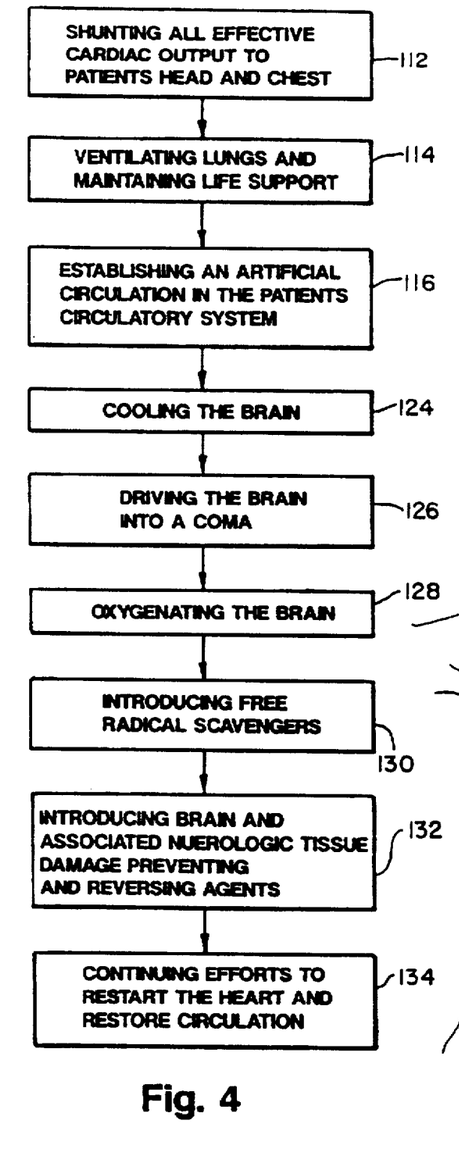
FIG. 4 is a flow chart of the method of the present invention.
Figure 5:
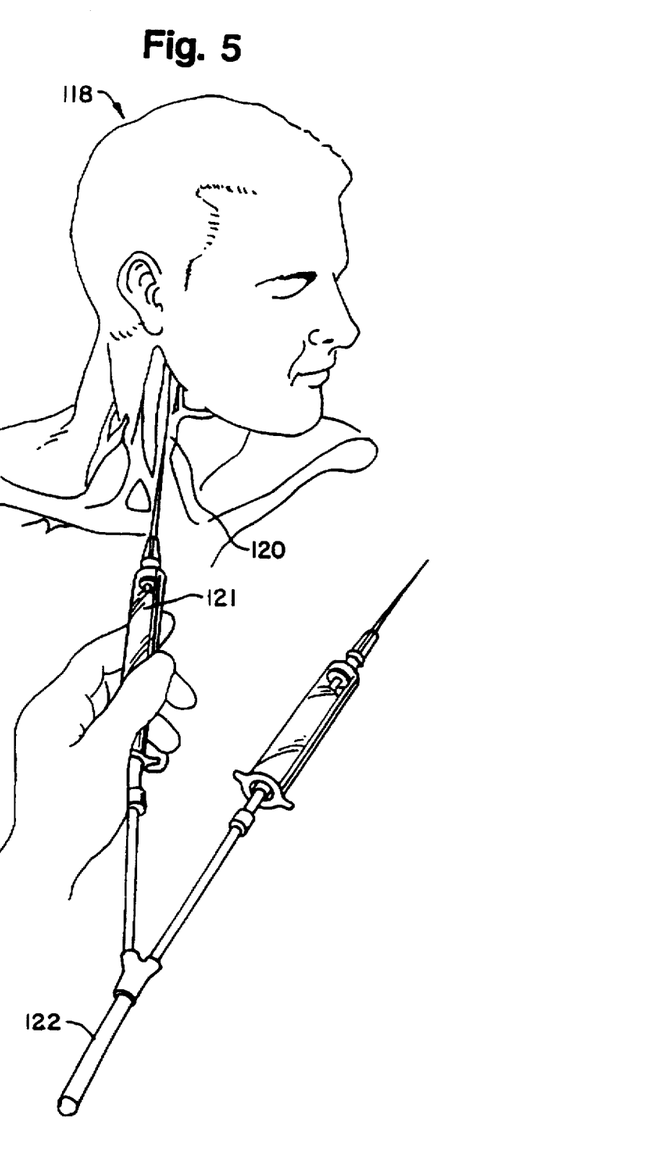
FIG. 5 is a front view of the patient being catheterized.

Reference is now made to FIGS. 4 and 5 which describe and show the non-invasive method of the invention for brain resuscitation. Preferably, this method involves the initial step of shunting all effective cardiac output away from the lower extremities and the abdomen 112 and toward the patient's heart and head at step 112. This shunting is preferably accomplished with mast trousers or pneumatic compression suits, which compress the lower abdomen and lower extremities forcing blood to the heart. However, other equivalent devices may be employed. During this time, the patient's lungs are ventilated with 100% oxygen along with basic cardiac life support or chest percussion and ventilation at step 114.

An artificial circulation through the brain is established at step 116 as the patient 118 is catheterized at an injection point along the circulatory system 120. The brain resuscitation solution enters the circulatory system through at least one blood vessel (artery or vein). Preferably, at least one external or internal carotid artery is catheterized. These carotid arteries are preferred since they are large arteries leading directly to the brain and can be easily found by feeling for the carotid pulse. Alternatively, any other blood vessel (artery or vein) may be the injection point catheterized. Such points include the femoral arteries, or jugular veins.

Balloon type catheters 121 with one way balloon valves at a distal point are preferred. Once inserted into the arteries, the balloons inflate, limiting any reverse blood and brain resuscitation fluid solution flow toward the heart through the artery.

Prior to catheterization, the catheter lines 122 are attached to the brain resuscitation device. This device is now activated and temperature-controlled (chilled) oxygenated brain resuscitation solution is delivered to the brain at step 124. This brain resuscitation solution is a mixture of various components suitable for treating these ischemic and anoxic injuries and keeping the brain and associated neurologic tissues intact. Specifically, the brain resuscitation solution is a fluid mixture containing barbiturates, oxygen carrying agents, antioxidants, Lazaroids, carrier vehicles, nutrients and other chemicals.

Initially the solution is temperature controlled, and delivered to the brain after having been chilled to approximately forty degrees F. At this temperature, the brain is hypothermically shocked and its metabolism, and subsequent free radical production is slowed. This temperature-controlling (cooling) step 124 may alone allow an additional thirty minutes of brain viability. Additional cooling is achieved by applying external cooling means to the patient's head. The cooling means includes bonnets containing ice cubes, synthetic cooling packets and the like. These bonnets may extend to cover the neck and spinal column.

Barbiturates comprise from about 0.000 to 20.00 percent by volume of the brain resuscitation solution. Preferably, the brain resuscitation solution includes 0.001 to 10.00 percent by volume of barbiturates. These barbiturates drive the brain into a submetabolic coma at step 126. Brain metabolism and subsequent free radical production are further lowered.

Thiopental is the preferred barbiturate. It has a fast induction time as it can cross the blood-brain barrier in three to seven seconds. Alternately, Secobarbital or Pentobarbital may be used.

Oxygen carrying agents comprise from about 0.00 to 99.90 percent by volume of this brain resuscitation solution. The preferred brain resuscitation solution includes 10.00 to 99.90 percent by volume of oxygen carrying agents. Perfluorocarbons are the preferred oxygen carrying agents, as they have an extremely high oxygen carrying capacity. When delivered to the brain, in this oxidation step 128, these perfluorocarbons are supersaturated with oxygen, having been oxygenated in the fluid reservoir. These perfluorocarbons act as a blood substitute, carrying oxygen to the brain similar to hemoglobin in the blood. These perfluorocarbons are temperature controlled and enter the patient's circulation at temperatures between 0 and 105 degrees F.

Antioxidants comprise from about 0.00 to 50.00 percent by volume of this brain resuscitation solution. Preferably, the brain resuscitation solution includes 0.001 to 30.00 percent by volume of antioxidants. These antioxidants are the preferred free radical scavengers. Once introduced into the brain at step 130, these antioxidants compete with brain tissue proteins as binding sites for the free radicals, mainly ionic $O_2^-$ Since a large portion of the free radicals complex with antioxidants, a substantial amount of free radical damage is prevented since these same free radicals do not bind and form complexes with proteins in the brain and associated neurologic tissues. The preferred antioxidants include Vitamin A, Vitamin B, Vitamin C, Vitamin E, Selenium Cystine, Cysteine, BHT, BHA, Hydergine and the like.

Lazaroids, an experimental drug class being developed by the Upjohn Co. of Kalamazoo, Mich., comprise about 0.00 to 30.00 percent by volume of the brain resuscitation solution. Preferably, Lazaroids comprise 0.001 to 20.00 percent by volume of the brain resuscitation solution. These Lazaroids are the preferred agents for protecting and reversing anoxic brain injury for up to forty-five minutes of anoxia, as shown in animal studies. These Lazaroids as well as nutrients, are introduced to the brain at step 132 in the brain resuscitation solution. Lazaroids are also free radical scavengers which fall under two major root moieties: pregnanes, ranging in molecular weight from roughly 580–720 and benzopyrans, ranging in molecular weight from 425–905.

The brain resuscitation solution may include up to 50 percent by volume of components which act as carrier vehicles and diluents for the antioxidants, barbiturates, perfluorocarbons and Lazaroids. Dimethylsulfoxide (DMSO) is the preferred carrier as it aids the above agents in traversing brain cell membranes. Additionally, the brain resuscitation solution may contain physiologic buffers to maintain pH.

Nutrients are also provided in this solution, up to 30 percent by volume. Glucose is one nutrient which is preferred.

Finally, the solution may contain up to 10 percent by volume of heparin or other suitable anti-blood coagulating agents to stop blood clotting which may occur due to lack of blood flow during the resuscitation attempt as a side effect of arterial system blockage and fluid backflow from the balloon tipped catheter.

Once this method has been performed and the brain resuscitation fluid has been properly administered, continuing efforts to restart the heart and restore the circulation at step 134 should be made.

Alternately, a method exists for use in emergency situations. In these situations, preoxygenated fluid may be directly injected into the patient's circulatory system. This is done by removing the reservoir canister from the brain resuscitation device and attaching it to a catheter line and then catheterizing the patient's circulatory system, or placing fluid from the reservoir canister into a syringe and injecting the patient.

The invention additionally discloses a method for preserving organs such as the heart, lungs, kidneys, pancreas and liver whereby they remain viable and suitable for harvesting and subsequent transplantation, in brain-dead patients or cadavers. This method can also be used to treat live (nonbrain-dead) patients, to preserve and resuscitate their organs. For example, these live patients may be suffering from ischemic injuries or other metabolic insults due to cardiac arrest, major trauma, suffocation, drowning, electrocution, blood loss and toxic poisoning from substances including carbon monoxide and cyanide.

The method involves establishing an artificial circulation for organ preservation and resuscitation solution (hereinafter "organ preservation solution") through the organ to be harvested (or preserved and/or resuscitated as with a live patient), as the patient is catheterized at an injection point. This injection point typically includes a major blood or lymph vessel, the organ itself, or tissues surrounding the organ. If a lymph vessel is catheterized, it should be in close proximity to the organ to be harvested. Preferably, arteries proximate to the organ are catheterized, as they can be found easily and provide a direct route to the organ.

Balloon-type catheters (similar or identical to those disclosed above) with one-way balloon valves at a distal point are preferred. Once inserted into the vessels of the circulatory system, the balloons inflate, limiting any reverse blood flow and organ preservation solution flow away from the organ to be harvested.

The invention also provides a method for preserving and/or resuscitating organs such as the heart, lungs, kidneys, pancreas, liver, intestines, stomach, esophagus and the like, whereby they remain viable and suffer minimal damage. The invention may be used to treat live patients, who suffer ischemic injury or other metabolic insults due to cardiac arrest, major trauma, suffocation, drowning, electrocution, blood loss and toxic poisoning from substances including carbon monoxide and cyanide. It may also be used on brain-dead patients and such that the organs would remain viable and suitable for harvesting and subsequent transplantation. This method involves the direct perfusion of body cavities such as the abdomen (abdominal or peritoneal cavity) and thorax (thoracic or chest cavity). This perfusion method involves filling the body cavities with the organ preservation solutions (disclosed below). The perfused organ preservation solution reaches the organs, tissues or vasculature associated with the organs through diffusion and/or other fluid adsorption processes.

The invention further provides a method for preserving and/or resuscitating organs such as the heart, lungs, kidneys, bladder, pancreas, liver, intestines, stomach, esophagus and the like, whereby they remain viable and suffer minimal damage. The invention may be used to treat live patients, who suffer ischemic injury or other metabolic insults due to cardiac arrest, major trauma, suffocation, drowning, electrocution, blood loss and toxic poisoning from substances including carbon monoxide and cyanide. It may also be used on brain-dead patients and cadavers to preserve the organs, such that they would remain viable and suitable for harvesting and subsequent transplantation. This method involves the direct infusion of cavities of the body, such as the gastro-intestinal (GI) tract, the respiratory tract, the urinary tract, the oral cavity, the nasal and sinus cavities, and any other spaces in the body in which fluid can be placed. This infusion method involves filling the cavities of the body with the organ preservation solutions (disclosed below). Entry into these cavities of the body is typically through body orifices, such as the mouth, nose, rectum, or urethra. The infused organ preservation solution is directly absorbed into the organs along the respective tracts as well as through diffusion and/or other fluid adsorption processes.

With body cavity perfusion, catheters, including the balloon type catheters and dual lumen (or multiple lumen) catheters disclosed above, specially designed catheters, tubes, cannulas, trocars, syringes, needles, or any equivalent delivery instruments may be used to instrumentize and deliver the organ preservation solutions (disclosed below) to perfuse the selected body cavity. The instrumentization (catheterization, cannulation or injection) involves piercing the skin at any point about the abdominal or thoracic cavities.

As with infusion of cavities of the body, catheters, including the balloon type catheters and dual lumen (or multiple lumen) catheters disclosed above, specially designed catheters, cannulas and tubes, such as nasal-gastric tubes, GI tubes, endotracheal tubes, or any equivalent delivery instruments may be used to instrumentize and deliver and infuse the organ preservation solutions (disclosed below) into the selected tracts (cavities of the body). Infusion is through any body orifice (e.g., mouth, nose, rectum or urethra) or passageway.

The organ preservation solutions (disclosed below) may be delivered to the body (perfused into body cavities or infused into cavities of the body), through the above-listed instruments (e.g., catheters, cannulas, needles, tubes, syringes, trocars, etc.), that are attached to the side opening or the terminal point of the organ preservation devices (disclosed above), from the reservoirs in the organ preservation devices. Once the devices are activated, delivery of temperature-controlled (chilled) oxygenated or non-oxygenated (unoxygenated) organ preservation solutions, for the above-disclosed methods, begins. The organ preservation solutions (disclosed below) are a mixture of various components suitable for keeping the organ(s) and tissues viable (and also resuscitating the organs in live, nonbrain-dead patients). Specifically, the organ preservation solutions are fluid mixtures that may include components such as oxygen carrying agents, antioxidants, Lazaroids, carrier vehicles, nutrients, cytoprotective agents and other chemicals. It is similar to that disclosed above for brain resuscitation except that barbiturates, which may be included, are not required as there is not a great need to induce a coma in a brain-dead patient or cadaver, nor a live patient here.

In the organ preservation methods disclosed above, the solution is temperature-controlled and delivered to the organ (s), tissues or vasculature associated with the organ(s), the body cavities (perfusion), or cavities of the body (infusion), after having been chilled below normal body temperature which may be to approximately 40 degrees F. At temperatures below normal body temperature, the degenerative metabolism of the organ(s) is slowed as the subsequent free radical production ($O_2^-$ or other free radicals) decreases. This temperature-controlling (cooling) step may alone allow up to an additional four hours of organ viability. The delivery of the chilled organ preservation solution may be continuous or pulsatile, cyclic or non-cyclic, depending upon the type of pump and logic control unit and organ preservation device (disclosed above).

With respect to pulsatile delivery, for the organ preservation methods disclosed above, the pump on the organ preservation device may be controlled to pump in both the forward and reverse directions. By pumping in both directions, organ preservation solution either 1) delivered into the major blood or lymph vessels, the organ itself, or tissues surrounding the organ, 2) delivered into the body cavity (i.e., perfusion), or 3) delivered into cavities of the body (i.e. infusion), could be returned through the catheter (or other similar cannula, tube or instrumentation) to the reservoir. Solution would then be returned from the reservoir to the organ(s), tissues or vasculature associated with the organ(s), the body cavities, or the cavities of the body, through subsequent pumping in a cyclic manner, for as long as desired. The combination of pulses from the pump could be determined by the operator of the organ preservation device, such that optimal circulation is based upon the volume and pressure capacity of the organ(s), the body cavity (as with body cavity perfusion), or cavities of the body (as with infusion).

For example, the pump could deliver a preset fluid volume, fluid at a preset pressure, or fluid at a preset flow rate, in a series of one or more pulses, to the 1) organ(s), tissues or vasculature associated with the organ(s), 2) the body cavity, or 3) cavities of the body. Once this fluid volume was delivered, the pump could be brought into reverse, either automatically or manually. This reversal would involve a series of one or more pulses to extract a volume approximately equivalent to that which was delivered, or other predetermined volume, back into the reservoir of the device. This cycle could continue for as long as desired, that is typically until organ harvesting begins (with brain-dead patients or cadavers), or until body function are restored (with live patients).

Since an organ preservation solution inflow, to the body, and solution outflow, back to the reservoir from the body, occurs, double lumen catheters (or multiple lumen catheters) are very useful. Alternately, the pump could be set to pulse only in a forward direction to inject the organ, peruse the body cavity, or infuse cavities of the body, in a non-cyclic manner.

Additional cooling is achieved by applying external cooling means to portions of the live or brain-dead patient or cadaver proximate to the organs being treated (in live patients) or to be harvested (as with brain-dead patients or cadavers. The cooling means include wraps containing ice cubes, synthetic cooling packets and the like.

With additional respect to the body cavity perfusion and infusion of the cavities of the body methods, additional circulation of the perfused organ preservation solution may be desired. This may be accomplished with external compressive garments or devices such as mast trouser-like pneumatic or hydraulic compressive body garments (placable anywhere along the body), or chest thumper type percussion devices, or other equivalent devices. Additionally, a pneumatic or mechanical device could be used to achieve a rocking motion of the body or the body cavity, thereby circulating and stirring the organ preservation solution within the body.

In one organ preservation solution, oxygen carrying agents comprise about 0.000 to 99.900 percent by volume of this organ preservation solution. The preferred organ preservation solution includes 10.000 to 99.000 percent by volume of oxygen carrying agents. Perfluorocarbons are the preferred oxygen carrying agents, as they have an extremely high oxygen capacity. When delivered to the organ, body cavity, or cavities of the body, in this oxygenation step, these perfluorocarbons may be supersaturated with oxygen, either having been oxygenated in the fluid reservoir, or preoxygenated prior to having been placed in the reservoir. These perfluorocarbons act as a blood substitute, carrying oxygen to the organ(s) similar to hemoglobin in the blood. Alternately, these oxygen carrying agents (e.g. perfluorocarbons) could be delivered to the body in a non-oxygenated state. These perfluorocarbons are temperature controlled and enter the patient's circulation at temperatures between 0° and 105° degrees F.

Antioxidants comprise from about 0.000 to 50.000 percent by volume of this organ preservation solution. Preferably, the organ preservation solution includes 0.001 to 30.000 percent by volume of antioxidants. These antioxidants are the preferred free radical scavengers. Once introduced into the organ(s), these antioxidants compete with organ tissue proteins as binding sites for the free radicals, mainly ionic $O_2^-$. Since a large portion of the free radicals complex with antioxidants, a substantial amount of free radical damage is prevented since these same free radicals do not bind and form complexes with proteins in the tissues forming the organ. The preferred antioxidants include Vitamin A, Vitamin B, Vitamin C, Vitamin E, Selenium, Cystine, Cysteine, BHT, BHA, Hydergine and the like.

Lazaroids, an experimental drug class being developed by the Upjohn Co. of Kalamazoo, Mich., comprise about 0.000 to 30.000 percent by volume of the organ preservation solution. Preferably, Lazaroids comprise 0.001 to 20.000 percent by volume of the organ preservation solution. These Lazaroids are the preferred agents for protecting and reversing anoxic injury for up to forty-five minutes of anoxia, as shown in animal studies. These Lazaroids, as well as nutrients, are introduced to the organ(s) as part of preserving the organ(s). Lazaroids are also free radical scavengers which fall under two major root moieties: pregnanes, ranging in molecular weight from roughly 580–720 and benzopyrans, ranging in molecular weight from 425–905.

The organ preservation solution may include up to 50.000 percent by volume of components which act as carrier vehicles and diluents for the antioxidants, perfluorocarbons and Lazaroids. Dimethylsulfoxide (DMSO) is the preferred carrier as it aids the above agents in traversing tissue cell membranes. Additionally, the organ preservation solution may contain physiologic buffers to maintain pH.

Nutrients are also provided in this solution, up to 30.000 percent by volume. Glucose is one nutrient which is preferred.

The solution may also include up to 20.000 percent by volume heavy metal scavengers or chelating agents. These heavy metal scavengers or chelating agents would also serve to inhibit free radical damage. Desferoxamine is one preferred heavy metal chelator.

Cytoprotective agents such as Calcium Channel Blockers ($Ca^{++}$) may also be present in this organ preservation solution in amounts up to 10.000 percent by volume. These cytoprotective agents, inhibit cell damage by stabilizing the cell membrane.

Additional metabolic mediators such as MK-801 and glutamate, aspartate or N-methyl-d-aspartate (NMDA) antagonists may also be in the solution up to 10.000 percent by volume.

Finally, the solution may contain up to 10.000 percent by volume of heparin or other suitable anti-blood coagulating agents to stop blood clotting which may occur due to lack of blood flow during the trauma, or due to the fact the patient is dead.

In another organ preservation solution, oxygen carrying agents comprise about 0.000 to 99.900 percent by volume of this organ preservation solution. The preferred organ preservation solution includes 10.000 to 99.000 percent by volume of oxygen carrying agents. Perfluorocarbons, hemoglobin based blood substitutes, or non-hemoglobin based blood substitutes are the preferred oxygen carrying agents, as they have an extremely high oxygen capacity. When delivered to the organ, in this oxygenation step, these oxygen carrying agents may be supersaturated with oxygen, either having been oxygenated in the fluid reservoir, or preoxygenated prior to having been placed in the reservoir. These perfluorocarbons, hemoglobin based blood substitutes, or non-hemoglobin based blood substitutes, act as blood substitutes, carrying oxygen to the organ(s) similar to hemoglobin in the blood. Alternately, these oxygen carrying agents (e.g. perfluorocarbons, hemoglobin based blood substitutes, or non-hemoglobin based blood substitutes) could be delivered to the body in a non-oxygenated state. These perfluorocarbons, hemoglobin based blood substitutes, or non-hemoglobin based blood substitutes are temperature controlled and enter the patient's circulation at temperatures between 0 and 105 degrees F.

Antioxidants comprise from about 0.000 to 50.000 percent by volume of this organ preservation solution. Preferably, the organ preservation solution includes 0.001 to 30.000 percent by volume of antioxidants. These antioxidants are the preferred free radical scavengers. Once introduced into the organ(s), these antioxidants compete with organ tissue proteins as binding sites for the free radicals. Since a large portion of the free radicals complex with antioxidants, a substantial amount of free radical damage is prevented since these same free radicals do not bind and form complexes with proteins in the tissues forming the organ. The preferred antioxidants include Vitamin A, Vitamin B, Vitamin C, Vitamin E, Selenium, Cystine, Cysteine, BHT, BHA, Hydergine and the like.

The organ preservation solution may include up to 99.000 percent by volume of components which act as carrier vehicles and diluents for the antioxidants and oxygen carrying agents (e.g., perfluorocarbons or hemoglobin based blood substitutes, or non-hemoglobin based blood substitutes). Dimethylsulfoxide (DMSO) or Normosol® (Abbott Laboratories, North Chicago, Ill.) are the preferred carriers as they aid the above agents in traversing tissue cell membranes.

Additionally, the organ preservation solution may contain physiologic buffers, such as HEPES (Monograph No. 4573, The Merk Index, Eleventh Edition) in amounts up to 50.000 percent by volume, to maintain pH.

Nutrients are also provided in this solution, up to 30.000 percent by volume. Glucose is one nutrient which is preferred.

The solution may also include up to 20.000 percent by volume heavy metal scavengers or chelating agents. These heavy metal scavengers or chelating agents would also serve to inhibit free radical damage.

Desferoxamine is one preferred heavy metal chelator.

Cytoprotective agents such as Calcium Channel Blockers ($Ca^{++}$) may also be present in this organ preservation solution in amounts up to 10.000 percent by volume. These cytoprotective agents, inhibit cell damage by stabilizing the cell membrane.

Ionotropic agents, such as epinephrine and dopamine, may be present in this solution up to 5.000 percent by volume.

Electrolytes, such as magnesium chloride, may be present in this solution up to 10.000 percent by volume.

Additional metabolic mediators such as MK-801 and glutamate, aspartate or N-methyl-d-aspartate (NMDA) antagonists may also be in the solution up to 10.000 percent by volume.

Finally, the solution may contain up to 10.000 percent by volume of heparin or other suitable anti-blood coagulating agents to stop blood clotting which may occur due to lack of blood flow during the trauma, or due to the fact the patient is brain-dead or a cadaver.

In brain-dead patients and cadavers, once these methods have been performed and the organ preservation solution has been properly administered, organ harvesting may begin. With respect to live patients, these methods may be performed as long as necessary until the trauma is controlled (e.g. the heart is restarted, body functions are restored) or other medical treatment is begun.

From the foregoing description, it is clear that those skilled in the art could make changes in the described embodiments and methods of the invention without departing from the broad inventive concepts thereof. It is understood, therefore, that this invention is not limited to the particular embodiments disclosed, but it is intended to cover any modifications which are within the spirit and scope of the claims.

What is claimed is:

1. A method for preserving organs other than the brain, comprising:

utilizing a control system to cool oxygenate and cool a solution to a temperature below body temperature, said the solution including free radical scavengers;

introducing the oxygenated, cooled solution into a mammalian body at an introduction point within said mammalian body and withdrawing the solution from said mammalian body;

whereby metabolic rates of said organs are slowed.

2. A method for preserving organs other than the brain, comprising:

oxygenating a solution;

cooling the solution to a temperature below body temperature; and introducing the oxygenated cooled solution into a mammalian body at an introduction point within said mammalian body, the introduction being through at least one lymph vessel;

whereby metabolic rates of said organs are slowed.

3. A method for preserving organs other than the brain in a mammalian body, comprising:

utilizing a control system to cool a solution to a temperature below body temperature; and introducing via a fluid path and pump system the cooled solution into a mammalian body at an introduction point within said mammalian body and withdrawing the solution from said mammalian body, the control system communicating with the pump system so as to control a rate of pumping, a direction of pumping and a mode of pumping;

whereby metabolic rates of said organs are slowed.

4. A method for preserving organs other than the brain in a mammalian body, comprising:

utilizing a control system to cool a solution to a temperature below body temperature; and introducing the cooled solution into a mammalian body at an introduction point within said mammalian body and withdrawing the solution from said mammalian body, said control system sensing and regulating fluid volume, pressure and temperature;

whereby metabolic rates of said organs are slowed.

5. A method for preserving organs other than the brain in a mammalian body, comprising:

utilizing a control system to cool a solution to a temperature below body temperature; and introducing the cooled solution into a mammalian body at an introduction point within said mammalian body and withdrawing the solution from said mammalian body, said control system sensing and displaying fluid flow rate and temperature for regulation thereof;

whereby metabolic rates of said organs are slowed.

6. A method for preserving organs other than the brain in a mammalian body, comprising:

utilizing a control system to cool a solution;

oxygenating the solution via an oxygenator; and introducing the oxygenated, cooled solution into a mammalian body at an introduction point within said mammalian body and withdrawing the solution from said mammalian body;

whereby metabolic rates of said organs are slowed.

7. A method for preserving organs other than the brain comprising:

a. providing a solution including free radical scavengers and oxygen carrying agents;

b. oxygenating said solution;

c. cooling said solution to a temperature below body temperature; and d. introducing said solution into a mamalian body at an introduction point within said body;

whereby metabolic rates of said organs are slowed.

8. The method of claim 7, wherein said introduction point is through at least one blood vessel.

9. The method of claim 7, wherein said introduction point is through at least one lymph vessel.

10. The method of claim 7, wherein said introduction point is through at least one of said organs or the tissue associated therewith.

11. The method of claim 7, wherein said oxygen carrying agents include perfluorocarbons.

12. The method of claim 7, wherein said free radical scavengers include antioxidants.

13. The method of claim 7, wherein said solution is cooled to approximately 40 degrees Fahrenheit.

14. The method of claim 7, additionally including the providing said solution with tissue protecting agents and tissue damage reversing agents.

15. The method of claim 14, wherein said tissue protecting agents and tissue damage reversing agents include Lazaroids.

16. A method for preserving organs other than the brain in a mammalian body, comprising:

utilizing a control system to oxygenate and cool a solution to a temperature below body temperature; and introducing the oxygenated, cooled solution into a mammalian body at an introduction point within said mammalian body and withdrawing the solution from said mammalian body;

whereby metabolic rates of said organs are slowed.

17. The method of claim 16, wherein said cooled solution includes perfluorocarbons.

18. The method of claim 16, wherein said solution is chilled to approximately 40 degrees Fahrenheit.

19. The method of claim 16, wherein said introduction point is through at least one blood vessel.

20. The method of claim 16, wherein said introduction point is through at least one of said organs or the tissue associated therewith.

21. A method for preserving an organ other than the brain in a mammalian body, comprising:

oxygenating the organ by introducing an oxygen carrying agent to the organ by means of an artificial circulation established by catheterization of the mammalian body;

lowering the temperature of the organ by introducing cooled fluid to the organ by means of an artificial circulation established by catheterization of the mammalian body; and inhibiting free radical damage in the organ by introducing a free radical scavenger to the organ by means of an artificial circulation established by catheterization of the mammalian body;

whereby metabolic rates of the organ are slowed.

22. The method of claim 21, wherein the oxygen carrying agent and free radical scavenger are introduced together in a solution.

23. The method of claim 21, wherein the cooled fluid for lowering the temperature of the organ comprises at least one of the oxygen carrying agent and the free radical scavenger.

24. The method of claim 21, wherein the oxygen carrying agent and free radical scavenger are administered through the same catheterization site.

25. The method of claim 21, wherein the oxygen carrying agent comprises a perfluorocarbon.

26. The method of claim 21, wherein the cooled fluid is cooled to a temperature of about 40 degrees Fahrenheit.

27. The method of claim 21, wherein the oxygen carrying agent is provided in a solution which is subjected to oxygenation prior to administration.

28. The method of claim 21, further comprising introducing a barbiturate to the organ by means of an artificial circulation established by catheterization of the mammalian body.

29. The method of claim 21, wherein the catheterization is carried out at a blood vessel, a lymph vessel, tissue surrounding the organ or the organ itself.

30. The method of claim 21, wherein the free radical scavenger comprises an antioxidant.

31. The method of claim 30, wherein the antioxidant is selected from the group consisting of Vitamin A, Vitamin B, Vitamin C, Vitamin E, Selenium, Cystine, Cysteine, BHT, BHA and Hydergine.

32. The method of claim 21, further comprising introducing to the organ at least one of a tissue protecting agent and a tissue damage reversing agent by means of an artificial circulation established by catheterization of the mammalian body.

33. The method of claim 32, wherein the oxygen carrying agent, free radical scavenger and tissue protecting agent or tissue damage reversing agent are introduced together in a solution.

34. The method of claim 32, wherein the tissue protecting agent or tissue damage reversing agent comprises a Lazaroid.

* * * * *